United States Patent [19]

Lynch

[11] 4,224,290

[45] Sep. 23, 1980

[54] PROCESS FOR RECYCLING CHEMICAL PLANT WASTE STREAMS CONTAINING RECOVERABLE CHLORINE

[75] Inventor: Richard W. Lynch, Chattanooga, Tenn.

[73] Assignee: Olin Corporation, New Haven, Conn.

[21] Appl. No.: 946,692

[22] Filed: Sep. 28, 1978

[51] Int. Cl.$^2$ ............................................... C01D 3/08
[52] U.S. Cl. ................................... 423/158; 423/165; 423/499
[58] Field of Search ................. 423/474, 165, 499, 158

[56] References Cited

U.S. PATENT DOCUMENTS

| | | | |
|---|---|---|---|
| 1,713,650 | 5/1929 | George et al. | 423/474 |
| 2,694,722 | 11/1954 | Katz | 260/453 |
| 3,134,641 | 5/1964 | Gleichert | 423/474 |
| 3,584,996 | 6/1971 | Hughes | 423/474 |

*Primary Examiner*—Wayne A. Langel

*Attorney, Agent, or Firm*—Gordon F. Sieckmann; Donald F. Clements

[57] ABSTRACT

Aqueous waste streams containing recoverable chlorine are reacted with an aqueous solution of an alkali metal hypohalite, such as sodium hypochlorite, to form an aqueous salt solution of an alkali metal halide, such as sodium chloride, and an alkaline earth metal hypohalite, such as calcium hypochlorite. Thereafter the aqueous salt solution is admixed with an organic alcohol to form an organic-aqueous salt solution. A gas containing chemically bound oxygen, such as carbon dioxide, is reacted with the organic-aqueous salt solution to form a slurry of solid particles of calcium carbonate suspended in a liquid mixture. The solid particles of calcium carbonate are separated from the liquid mixture.

The aqueous phase containing sodium chloride may be recycled for use as a reactant in a chlor-alkali electrolytic cell. The organic phase containing organic hypochlorite may be used as a chlorinating agent or may be treated with an acid, such as hydrochloric acid, to reclaim free chlorine.

38 Claims, No Drawings

PROCESS FOR RECYCLING CHEMICAL PLANT WASTE STREAMS CONTAINING RECOVERABLE CHLORINE

This invention is a process for recovering recoverable chlorine from aqueous waste streams as an organic hypohalite and an alkali metal halide.

Several chemical and electrochemical processes of preparing organic hypohalites are taught by the prior art.

For example, U.S. Pat. No. 2,694,722, issued Nov. 16, 1954, to Irving Katz, discloses a chemical process for preparing alkyl hypochlorites which comprises dissolving an inorganic hypochlorite salt such as sodium hypochlorite and an organic alcohol such as tertiary butyl alcohol in water and then adding carbon dioxide as shown by equation (1):

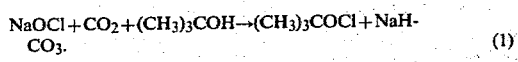

$$NaOCl + CO_2 + (CH_3)_3COH \rightarrow (CH_3)_3COCl + NaHCO_3. \quad (1)$$

In *Encyclopedia of Chemical Technology*, by Kirk-Othmer, 2nd edition, volume 5, pages 24–25, a variety of chemical processes are employed for preparing organic hypochlorites. Reference is made to solutions prepared with carbon tetrachloride, chloroform, or o-dichlorobenzene.

In another example, U.S. Pat. No. 3,449,225, issued to Edwin A. Matzner on June 10, 1969, an electrolytic process is disclosed for preparing organic hypohalites from inorganic halides and organic compounds.

There is also a long felt need at the present time for economical low energy process for purifying waste streams containing high concentrations of available chlorine so that such streams thereafter may suitably contact activated carbon beds in municipal effluent treatment plants.

There is also a long felt need at the present time to operate chemical plants which produce recoverable chlorine compounds by maximizing recycle and minimizing discharge of aqueous chemical plant waste streams in view of the strong environmental protection position of federal and state governments.

There is also a long felt need for an economical process of recovering recoverable chlorine in the waste streams of chemical plants which produce alkali metal halides, alkaline earth hypochlorites and the like.

OBJECTS

It is a primary object of this invention to provide a process for economically recovering the recoverable chlorine in waste streams formed in chemical plants which produce alkali metal halides, alkaline earth hypohalites and the like.

It is a further object of the invention to provide a process for modifying waste streams formed in plants used in the production of calcium hypochlorite in order to permit contact between these purification streams and activated carbon beds employed in water purification systems.

An additional object of the invention is to provide a process for treating waste streams produced in calcium hypochlorite plants thereby minimizing the amount of material required to be processed in waste treatment plants.

These and other objects of the invention will be apparent from the following detailed description and the appended claims.

BRIEF DESCRIPTION OF THE INVENTION

It has now been discovered that the foregoing objects are accomplished in a process for recovering recoverable chlorine from aqueous waste streams by converting the recoverable chlorine to an organic hypohalite and an alkali metal halide.

The process of this invention comprises reacting the aqueous solution containing recoverable chlorine with an alkali metal hypohalite, such as sodium hypochlorite, to form an aqueous salt solution containing sodium chloride, sodium hypochlorite and calcium hypochlorite. The aqueous salt solution is admixed with an organic alcohol to form an aqueous-organic salt solution which is reacted with a gas containing chemically bound oxygen, such as carbon dioxide, to form a slurry. The slurry is comprised of solid particles of calcium carbonate suspended in a liquid mixture in an aqueous phase and organic phase, containing calcium carbonate, organic hypochlorite, sodium bicarbonate, organic alcohol, organic solvent, sodium hypochlorite, sodium chloride, sodium chlorate, and water. The solid particles of calcium carbonate are separated from the liquid mixture.

The solid particles of calcium carbonate cake are disposed of as waste or otherwise utilized.

Thereafter the remaining liquid mixture is further separated to form an aqueous phase containing sodium chloride, sodium hypochlorite, sodium chlorate, and sodium bicarbonate, and an organic phase containing organic hypochlorite, organic alcohol and organic solvent.

The aqueous phase may be used as an electrolyte in a chlor-alkali cell after appropriate purification and salt concentration adjustment.

The organic phase containing organic hypochlorite may be used as a chlorinating agent.

DETAILED DESCRIPTION OF THE INVENTION

A typical waste stream which may be treated according to the process of this invention is one that contains recoverable chlorine as produced as a plant effluent in chemical plants used in the preparation of calcium hypochlorite. The process of this invention will be described as it is applied to the purification of such effluent. However, those skilled in the art will recognize that the same treatment may be applied to other recoverable chlorine waste streams of the type produced in alkali metal hypochlorite plants such as sodium hypochlorite plants, other alkaline earth metal hypochlorites and the like.

As indicated in *Encyclopedia of Chemical Technology*, by Kirk-Othmer, 2nd edition, volume 5, pp. 16–25, a variety of chemical processes are employed for preparing calcium hypochlorite. Each plant effluent from these processes will have a different detailed analysis, depending upon the reaction used in the preparation of calcium hypochlorite, the efficiency of the process, and the plant operation. However, each will have an excess of recoverable chlorine in the form of calcium hypochlorite, sodium hypochlorite or a mixture of calcium hypohalite and sodium hypohalite. A typical analysis of such an effluent from a typical calcium hypochlorite plant is illustrated as follows:

| Component | Typical Analysis | Min./Max. Analysis |
|---|---|---|
| Ca(OCl)$_2$ | 18 grams per liter | 4 to 80 gpl |
| NaCl | 60 grams per liter | 25 to 200 gpl |
| Ca(OH)$_2$ | 2 grams per liter | 1 to 10 gpl |
| Ca(ClO$_3$)$_2$ | 3 grams per liter | 1 to 15 gpl |
| CaCl$_2$ | 35 grams per liter | 1 to 200 gpl |

Because of the solubility characteristics of calcium hypochlorite and any occasional spills occurring during processing, it is extremely difficult to economically remove all the calcium hypochlorite from the waste stream effluent, and as a result, the chemical analyses of the waste stream effluent will vary as indicated above.

Presently the calcium hypochlorite contained in streams treated in municipal waste treatment plants is required by law to be chemically or thermally decomposed before the effluent stream is permitted to contact activated carbon beds.

To simplify the description, the invention will be defined in terms of "recoverable chlorine." However, for purposes of the process of this invention the term "recoverable chlorine" also includes (i) alkaline earth metal halides such as calcium chloride, calcium bromide, and mixtures thereof; (ii) alkaline earth metal hypohalites such as calcium hypochlorites, calcium hypobromites, and mixtures thereof; (iii) alkaline earth metal chlorates such as calcium chlorate; (iv) alkali metal hypohalites such as sodium hypochlorite, sodium hypobromite, and mixtures thereof; and (v) mixtures of alkaline earth metal halides, alkaline earth metal hypohalites, alkaline earth metal chlorates, alkali metal hypohalites mentioned above and mixtures thereof.

In the process of this invention, the impure aqueous solution described above, containing recoverable chlorine is reacted with an aqueous solution of an alkali metal hypohalite such as, an aqueous solution comprised of sodium hypochlorite in the range of about 5 to about 35% by weight, and preferably in the range from about 7 to about 32% by weight.

One skilled in the art will recognize that the term "alkali metal hypohalite" includes potassium hypochlorite, potassium hypobromite, sodium hypochlorite, sodium hypobromite, and mixtures thereof.

The sodium hypochlorite employed in the process of this invention may be produced chemically, for example, by reacting sodium hydroxide with chlorine to produce sodium hypochlorite and sodium chloride. One skilled in the art will recognize that any suitable technique for the preparation of aqueous sodium hypochlorite solution will suffice for the purpose of this invention.

Since aqueous solutions of sodium hypochlorite are generally produced in chemical plants producing alkali metal hypochlorites and alkaline earth metal hypochlorites, the process of this invention employs a reactant which is readily available in plants which produce the waste streams to be treated.

Additionally, one skilled in the art will recognize that the presence of an alkali metal halide, such as sodium chloride, in the alkali metal hypohalite solution is not a strict requirement of this invention, but will recognize that alkali metal halides, such as sodium chloride, are expected components in the impure waste streams of a typical chemical plant producing alkali metal hypohalites, alkaline earth metal hypohalites, and the like.

In a first reaction step of the process of this invention, recoverable chlorine, as for example an alkaline earth metal chloride, such as calcium chloride, present in the impure aqueous solution reacts with an alkali metal hypohalite, such as sodium hypochlorite, to form sodium chloride and calcium hypochlorite according to equation (2):

$$CaCl_2 + 2NaOCl \rightarrow 2NaCl + Ca(OCl)_2 \qquad (2)$$

Although calcium chloride is generally present in the impure aqueous stream previously described, one skilled in the art will recognize that in the absence of calcium chloride, treatment of the impure aqueous stream with the alkali metal hypohalite, such as sodium hypochlorite, is unnecessary.

The temperature of the reaction as represented by equation (2) is in the range from about 10° C. to about 50° C. and preferably from about 20° C. to about 40° C.

The molar ratio of alkali metal hypohalite such as sodium hypochlorite to alkaline earth metal halide such as calcium chloride is in the range from about 2:1 to about 10:1 and preferably from about 2.5:1 to about 3:1 to ensure complete conversion of the alkaline earth metal halide such as CaCl$_2$, which is generally stoichiometric.

The reaction time required for completion of the reaction described in equation (2) is in the range from about 5 to about 60 minutes and preferably from about 10 to about 40 minutes.

The reaction products, sodium chloride and calcium hypochlorite, are formed in an aqueous salt solution comprised of sodium chloride, sodium hypochlorite, calcium hypochlorite with the remainder essentially water.

In a second step of the process of this invention, the aqueous salt solution is mixed with an organic alcohol and preferably an organic solvent to form an organic-aqueous salt solution.

The time required for adequate mixing of the aqueous salt solution with the organic alcohol and the organic solvent is in the range from about 1 to about 35 minutes, preferably from about 3 to about 15 minutes.

Any organic alcohol capable of being chemically transformed into the corresponding organic hypohalite may be utilized in the process of this invention. It has been found convenient to employ those organic alcohols which are liquid at the processing temperatures herein described.

Examples of alcohols which may be employed as hypohalite carriers in this process are secondary alcohols of the formula,

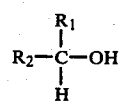

where R$_1$ and R$_2$ are each selected from a group consisting of alkyl and aryl groups having 1 to about 10 carbon atoms each. Examples of secondary alcohols are 2-propanol, 2-butanol, 2-pentanol, 3-pentanol, 2-methyl-3-butanol, 3-hexanol, 2-hexanol, 2-methyl-3-pentanol, 3-methyl-2-pentanol, 2-methyl-4-pentanol, 2,2-dimethyl-3-butanol, 2-heptanol, 3-heptanol, 4-heptanol, 2-methyl-3-hexanol, 2-methyl-4-hexanol, 2-methyl-5-hexanol, 2,2-dimethyl-3-pentanol, 2,2-dimethyl-4-pentanol, 3,3-dimethyl-2-pentanol, 2,4-dimethyl-3-pentanol, 2,3- dimethyl-4-pentanol, 3-ethyl-2-pentanol, 2-octanol, 2-nonanol, 2-decanol, and 4-decanol.

Other alcohols employed may be tertiary diols of the formula,

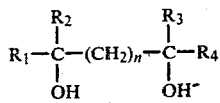

where n is an integer from 1 to about 10 and $R_1$, $R_2$, $R_3$ and $R_4$ are each selected from a group consisting of alkyl and aryl groups having 1 to about 10 carbon atoms each. Preferred tertiary diols of this type are 2,5-dimethyl-2,5-hexanediol, 2,4-dimethyl-2,4-pentanediol, 2,4-dimethyl-2,4-hexanediol, and 2-methyl-4-ethyl-2,4-hexanediol.

Other examples of alcohols which may be used in this process are tertiary alcohols of the formula,

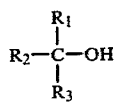

where $R_1$, $R_2$, and $R_3$ are each selected from a group consisting of alkyl and aryl groups having 1 to about 10 carbon atoms each. Tertiary alcohols of this type are 2-methyl-2-propanol (tertiary butyl alcohol), 2-methyl-2-butanol (tertiary amyl alcohol), 3-methyl-3-pentanol, 2-methyl-2-pentanol, 3-ethyl-3-pentanol, 3-isopropyl-3-pentanol, 2,3-dimethyl-3-pentanol, 2,3-dimethyl-2-pentanol, 3-ethyl-3-octanol, 5-butyl-5-nonanol, 3,7-dimethyl-3-octanol, 2-methyl-2-octanol, 4-ethyl-4-heptanol, 2-methyl-2-heptanol, 3-methyl-3-heptanol, 4-methyl-4-heptanol, 4-propyl-4-heptanol, 3-ethyl-3-hexanol, 3-ethyl-5-methyl-3-hexanol, 2-methyl-2-hexanol, 3-methyl-3-hexanol, 2,3,5-trimethyl-2-hexanol, 2,3,4-trimethyl-2-hexanol, 2,2,3-trimethyl-3-hexanol, 2,3,5-trimethyl-3-hexanol, 3,4,4-trimethyl-3-hexanol, 3,5,5-trimethyl-3-hexanol, 2,4-dimethyl-2-pentanol, 3-ethyl-2-methyl-3-pentanol, 2-phenyl-2-pentanol, 3-phenyl-3-pentanol, 2,4,4-trimethyl-2-pentanol, 2,3-dimethyl-2-butanol, 2,3,3-trimethyl-2-butanol, and triphenylmethanol.

To simplify the description, the invention will be defined in terms of "organic alcohol", but one skilled in the art will recognize that the term "organic alcohol" also includes mixtures of organic alcohols.

As used throughout the description and claims, the term "alkyl" is intended to include straight chain, cyclic, substituted straight chain and substituted cyclic alkyl groups. As used throughout the description and claims, the term "aryl" is intended to include normal and substituted aromatic groups.

In a preferred embodiment of the invention, an organic solvent other than the organic alcohol is used which may be an essentially inert liquid essentially immiscible with water.

The proportion of organic solvent will vary with the nature of the organic solvent and the organic hypochlorite, but sufficient organic solvent is present at all times to extract the maximum proportion of organic hypochlorite from the aqueous solution.

Suitable solvents include a wide variety of halogenated hydrocarbons and organic phosphate compounds. A typical family of halogenated hydrocarbon solvents are those represented by the formula,

where $x+y=4$ and y is an integer from 2 to 4.

Examples of suitable members of this family of solvents include $CCl_4$, $CHCl_3$, and $CH_2Cl_2$.

Another example of an organic solvent is an organic phosphate of the formula,

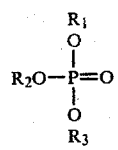

where $R_1$, $R_2$, and $R_3$ are each selected from a group consisting of alkyl and aryl groups, for example, methyl, ethyl, n-butyl, isopropyl, n-pentyl, isobutyl, n-propyl, phenyl, 2-tolyl, 3-tolyl, or 4-tolyl. In general, each separate alkyl or aryl group will have 1 to about 10 carbon atoms. Preferred organic phosphates of this type are tri-methyl phosphate, tri-ethyl phosphate, tri-n-butyl phosphate, tri-n-propyl phosphate, tri-isopropyl phosphate, tri-n-pentyl phosphate, tri-isobutyl phosphate, tri-phenyl phosphate, tri-2-tolyl phosphate, tri-3-tolyl phosphate and tri-4-tolyl phosphate, tri-n-propyl phosphate, tri-isopropyl phosphate, tri-n-pentyl phosphate, tri-isobutyl phosphate, tri-phenyl phosphate, tri-2-tolyl phosphate, tri-3-tolyl phosphate and tri-4-tolyl phosphate.

Another example of a suitable organic solvent family is of the formula,

where y is an integer from 2 to 6 and $x+y=6$.

Examples of this family include 1,1,1-trichloro-2,2,2-trifluoroethane, hexachloroethane, and fluoropentachloroethane.

Another example of a suitable family of organic solvents is of the formula,

where y is an integer from 1 to 6 and $x+y=6$.

Examples of this family include 1,2-dichloroethane, 1,1,1-trichloroethane, 1,1,2-trichloroethane, 1,1,1,2-tetrachloroethane, 1,1,2,2-tetrachloroethane, and pentachloroethane.

Another example of a suitable family of organic solvents is of the formula,

where y is an integer from 1 to 2 and $x+y=6$. Examples are 1,2-difluoroethane, 1,1-difluoroethane, and fluoroethane.

Another example of a suitable family of organic solvents is of the formula,

where y is an integer from 1 to about 4 and $x+y=8$.

Examples of this family include isopropyl chloride, 1,2-dichloropropane, 1,1,1,2-tetrachloropropane, and 1,1,2,2-tetrachloropropane.

Another example of a suitable family of organic solvents is a tertiary halide of the formula,

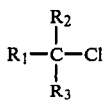

where $R_1$, $R_2$, and $R_3$ are each selected from a group consisting of alkyl and aryl groups having from 1 to about 10 carbon atoms each. Solvents include 2-chloro-2-methylpropane, 2-chloro-2-methylbutane, 2-chloro-2-methylpentane, and 3-chloro-3-ethylpentane.

Other examples of suitable organic solvents include 2-chlorotoluene, 3-chlorotoluene, 4-chlorotoluene, and alpha-chlorotoluene.

Yet other solvents which may be used include chlorobenzene, 1,2-dichlorobenzene, 1,3-dichlorobenzene, 1,2,4-trichlorobenzene, and fluorobenzene.

To simplify the description, the invention will be defined in terms of "organic solvent", but one skilled in the art will recognize that the term "organic solvent" also includes the mixtures of organic solvents.

In a third step of the process of this invention, a gas containing chemically bound oxygen, such as carbon dioxide, reacts with the alkaline earth hypohalite, such as calcium hypochlorite, and the organic alcohol, for example, tertiary butyl alcohol, in the organic aqueous salt solution to form tertiary butyl hypochlorite, calcium carbonate, and water according to equation (3):

$$Ca(OCl)_2 + 2(CH_3)_3COH + CO_2 \rightarrow 2(CH_3)_3COCl + CaCO_3 + H_2O \quad (3)$$

However, other gases containing chemically bound oxygen, such as $SO_3$, may be employed in the process of this invention.

In another embodiment of the invention carbon dioxide is added simultaneously with the alcohol and organic solvent, if employed, to the aqueous salt solution.

Carbon dioxide reacts with sodium hypochlorite and the organic alcohol, for example, tertiary butyl alcohol, to form tertiary butyl hypochlorite and sodium bicarbonate as per equation (4):

$$NaOCl + (CH_3)_3COH + CO_2 \rightarrow (CH_3)_3COCl + NaHCO_3 \quad (4)$$

The temperature and pressure conditions are the same for reaction (3) and reaction (4) as for reaction (2).

The chemical equivalent ratio of carbon dioxide to total calcium hypochlorite and sodium hypochlorite present in the reaction zone is in the range from about 1:1 to about 20:1, and preferably from about 1.5:1 to about 5:1 to ensure maximum conversion of hypochlorite species.

The chemical equivalent ratio of organic alcohol to total calcium hypochlorite and sodium hypochlorite is in the range from about 1:1 to about 10:1, and preferably from 2:1 to about 5:1.

The time required for the completion of reaction (3) and reaction (4) is in the range from about 5 minutes to 180 minutes, and preferably from about 15 minutes to about 120 minutes.

After completion of reaction (3) and reaction (4) a slurry forms of solid $CaCO_3$ suspended in a liquid mixture of aqueous and organic phases, containing calcium carbonate, organic hypochlorite, sodium bicarbonate, organic alcohol, organic solvent, sodium hypochlorite and sodium chloride and water.

Solid calcium carbonate is separated from the liquid mixture by any suitable solid-liquid separation technique such as filtration, centrifuging, settling, and the like. Filtration is the preferred form of solid-liquid separation, and the invention will be described using filtration as the solid-liquid separation technique. One skilled in the art will recognize that any other suitable solid-liquid separation technique may be employed.

The filtration temperature is in the range from about 10° C. to about 50° C. and preferably from about 20° C. to about 40° C.

The filtration pressure is essentially atmospheric but may be super or subatmospheric.

Filtration of the slurry of solid calcium carbonate suspended in the liquid mixture of an aqueous phase and an organic phase, results in the formation of a filter cake and a filtrate. The filter cake is comprised of calcium carbonate and a minimal amount of residual filtrate. The resulting cake may be disposed of as waste or otherwise utilized.

If desired, residual filtrate is removed from the filter cake by any conventional technique such as washing the filter cake with a suitable solvent or by passing the filter cake through an evaporator under suitable pressure and temperature conditions to evaporate the organic materials. The evaporated organic materials are condensed and conveyed to intermediate storage for reuse in the first reaction step of the process of this invention.

The difference between the density of the organic phase which contains organic hypochlorite, organic alcohol, and organic solvent, and the density of the aqueous phase, which contains sodium bicarbonate, sodium hypochlorite, and sodium chloride, is preferably of at least sufficient magnitude so that physical phase separation can be practiced by methods recognized by those skilled in the art. Large density differences facilitate easy separation of the organic phase from the aqueous phase by conventional phase separation techniques.

The organic phase is used as a chlorinating agent or may be treated with an acid such as hydrochloric acid, to recover free chlorine.

The aqueous phase is comprised of sodium bicarbonate in the range of about 1 to 10% by weight, sodium chloride in the range from about 1 to 25% by weight, with the remainder being essentially water. After brine reconstitution and purification, the aqueous phase may be used as reactant in a chlor-alkali cell or may be sent to waste treatment as effluent.

The process herein disclosed permits recycle of aqueous streams containing recoverable chlorine, by converting the recoverable chlorine to an organic hypochlorite and an alkali metal chloride.

By treating waste streams produced in calcium hypochlorite plants, the process of this invention minimizes the amount of material required to be processed in waste treatment plants.

The following examples are presented to define the invention more fully without any intention of being limited. All parts and percentages are by weight unless otherwise specified.

EXAMPLE 1

In a reactor about 70 parts of a first solution whose composition corresponding to a typical calcium hypochlorite plant effluent analysis was reacted with agitation into a second solution, about 30 parts of an aqueous sodium hypochlorite solution.

The first solution was comprised of:

| COMPONENT | PERCENT |
|---|---|
| $Ca(OCl)_2$ | 7.32 |
| $Ca(OH)_2$ | 0.21 |
| $CaCl_2$ | 5.05 |
| NaCl | 13.45, | the remainder being essentially water.

The second solution, an aqueous sodium hypochlorite solution, was found by analysis to contain:

| COMPONENT | PERCENT |
|---|---|
| NaOCl | 9.18 |
| NaCl | 20.16 |
| NaOH | 0.02, | the remainder being essentially water.

About 100 parts carbon tetrachloride and 20 parts tertiary amyl alcohol were added to the reaction contents.

As the resulting mixture was agitated, carbon dioxide was bubbled slowly through the resulting mixture for about 30 minutes, and the resulting slurry was then filtered.

The filter cake (about 15.8 parts) was found by analysis to contain:

| COMPONENT | PERCENT |
|---|---|
| $Ca(OCl)_2$ | 0.83 |
| $Ca(OH)_2$ | 28.47 |
| $CaCl_2$ | 0.92 |
| NaCl | 3.99, | with the remainder being essentially water.

The remaining filtrate physically separated into two phases, an organic phase (about 240 parts) atop an aqueous phase (about 123 parts).

The aqueous phase was found by analysis to contain:

| COMPONENT | PERCENT |
|---|---|
| NaOCl | 0.17 |
| $Ca(OH)_2$ | 0.008 |
| NaCl | 17.12 |
| NaOH | 0.30 | with the remainder being essentially water.

The organic phase contained about 15 parts tertiary amyl hypochlorite.

The percent conversion of sodium hypochlorite, defined as 100 times the ratio of chemical equivalents of sodium hypochlorite reacted to form sodium hypochlorite to the total chemical equivalents sodium hypochlorite originally added, was about 96.7%.

The percent yield of tertiary amyl hypochlorite, defined as 100 times the ratio of chemical equivalents tertiary amyl hypochlorite formed to the chemical equivalents sodium hypochlorite and calcium hypochlorite used, was about 89.1%.

What is claimed is:

1. A process for recovering organic hypohalite and alkali metal halide from an impure aqueous solution containing alkaline earth metal halide and alkaline earth metal hypohalite which comprises:
   (a) reacting said impure aqueous solution with alkali metal hypohalite to form an aqueous salt solution, wherein the molar ratio of said alkali metal hypohalite to said alkaline earth metal halide is in the range from about 2:1 to about 10:1;
   (b) admixing said aqueous salt solution with an organic alcohol to form an organic-aqueous salt solution;
   (c) reacting a gas containing chemically bound oxygen with said organic-aqueous salt solution to form a slurry of solid particles suspended in a liquid mixture of an organic phase and an aqueous phase;
   (d) separating said solid particles from said liquid mixture;
   (e) separating said liquid mixture into an aqueous phase and an organic phase;
   (f) said aqueous phase predominating in alkali metal halide; and
   (g) said organic phase predominating in organic hypohalite.

2. The process of claim 1, wherein said alkaline earth metal halide is calcium halide.

3. The process of claim 2, wherein said calcium halide is calcium chloride.

4. The process of claim 3, wherein said alkaline earth metal hypohalite is calcium hypohalite.

5. The process of claim 4, wherein said calcium hypohalite is calcium hypochlorite.

6. The process of claim 5, wherein said alkali metal hypohalite is sodium hypohalite.

7. The process of claim 6, wherein said sodium hypohalite is sodium hypochlorite.

8. The process of claim 7, wherein said gas containing chemically bound oxygen is carbon dioxide and wherein said solid particles are comprised of calcium carbonate.

9. The process of claim 7, wherein the temperature of the process is in the range from about 10° C. to about 50° C.

10. The process of claim 9, wherein the temperature of the process is in the range from about 20° C. to about 40° C.

11. The process of claim 10, wherein the molar ratio of sodium hypochlorite to said calcium chloride of said impure aqueous stream is in the range from about 2:1 to about 10:1.

12. The process of claim 11, wherein the molar ratio of sodium hypochlorite to said calcium chloride of said impure aqueous stream is in the range from about 2.5:1 to about 3:1.

13. The process of claim 12, wherein the chemical equivalent of said carbon dioxide to said total calcium hypochlorite and said sodium hypochlorite is in the range from about 1:1 to about 20:1.

14. The process of claim 13, wherein the chemical equivalent of said carbon dioxide to said total calcium hypochlorite and said sodium hypochlorite is in the range from about 1.5:1 to about 5:1.

15. The process of claim 14, wherein the chemical equivalent ratio of said organic alcohol to total calcium hypochlorite and sodium hypochlorite is in the range from about 1:1 to about 10:1.

16. The process of claim 15, wherein the chemical equivalent ratio of said organic alcohol to total calcium hypochlorite and sodium hypochlorite is in the range from about 2:1 to about 5:1.

17. The process of claim 16, wherein said organic alcohol is a secondary alcohol of the formula, $$R_2-\underset{\underset{H}{|}}{\overset{\overset{R_1}{|}}{C}}-OH$$

where $R_1$ and $R_2$ are each selected from a group consisting of separate alkyl and aryl groups having 1 to about 10 carbon atoms each.

18. The process of claim 16, wherein said organic alcohol is a tertiary diol of the formula, $$R_1-\underset{\underset{OH}{|}}{\overset{\overset{R_2}{|}}{C}}-(CH_2)_n-\underset{\underset{OH}{|}}{\overset{\overset{R_3}{|}}{C}}-R_4$$

where n is an integer from 1 to about 10 and $R_1$, $R_2$, $R_3$, and $R_4$ are each selected from a group consisting of separate alkyl and aryl groups having 1 to about 10 carbon atoms each.

19. The process of claim 16, wherein said organic solvent is 1,2-dichlorobenzene.

20. The process of claim 11, wherein said organic solvent is selected from a group consisting of 2-chlorotoluene, 3-chlorotoluene, 4-chlorotoluene, and alpha-chlorotoluene.

21. The process of claim 16, wherein said organic solvent is selected from the group consisting of chlorobenzene, 1,2-dichlorobenzene, 1,3-dichlorobenzene, 1,2,4-trichlorobenzene, and fluorobenzene.

22. The process of claim 16, wherein said organic alcohol is a tertiary alcohol of the formula, $$R_2-\underset{\underset{R_3}{|}}{\overset{\overset{R_1}{|}}{C}}-OH$$

where $R_1$, $R_2$, and $R_3$ are each selected from a group consisting of separate alkyl and aryl groups having 1 to about 10 carbon atoms each.

23. The process of claim 22, wherein said organic alcohol is tertiary butyl alcohol.

24. The process of claim 22, wherein said organic alcohol is tertiary amyl alcohol.

25. The process of claim 22, wherein said organic alcohol is 3-methyl-3-pentanol.

26. The process of claim 22, wherein said organic alcohol is cyclohexanol.

27. The process of claim 1, wherein an essentially inert organic solvent essentially immiscible with water is admixed with said alcohol.

28. The process of claim 27, wherein said organic solvent is of the formula, $$CH_xCl_y$$

where $x+y=4$ and y is an integer from 2 to 4.

29. The process of claim 29, wherein said organic solvent is $CCl_4$.

30. The process of claim 27, wherein said organic solvent is of the formula, $$C_2F_xCl_y$$

where y is an integer from 2 to 6 and $x+y=6$.

31. The process of claim 27, wherein said organic solvent is tertiary butyl chloride.

32. The process of claim 27, wherein said organic solvent is of the formula, $$C_2H_xCl_y$$

where y is an integer from 1 to 6 and $x+y=6$.

33. The process of claim 27, wherein said organic solvent is of the formula, $$C_2H_xF_y$$

where y is an integer from 1 to 2 and $x+y=6$.

34. The process of claim 27, wherein said organic solvent is of the formula, $$C_3H_xCl_y$$

where y is an integer from 1 to about 4 and $x+y=6$.

35. The process of claim 27, wherein said organic solvent is a tertiary halide of the formula, $$R_1-\underset{\underset{R_3}{|}}{\overset{\overset{R_2}{|}}{C}}-Cl$$

where $R_1$, $R_2$, and $R_3$ are each selected from a group consisting of separate alkyl and aryl groups having from 1 to about 10 carbon atoms each.

36. The process of claim 27, wherein said organic solvent is an organic phosphate of the formula, $$R_2O-\underset{\underset{R_3}{\underset{|}{O}}}{\overset{\overset{R_1}{\overset{|}{O}}}{P}}=O$$

where $R_1$, $R_2$, and $R_3$, are each selected from a group consisting of separate alkyl and aryl groups each having 1 to about 10 carbon atoms each.

37. The process of claim 1, wherein said gas containing chemically bound oxygen is sulfur trioxide.

38. The process of claim 31, wherein said organic phase is treated with hydrochloric acid to reclaim free chlorine.

* * * * *